United States Patent
Lin et al.

(10) Patent No.: US 12,048,682 B2
(45) Date of Patent: *Jul. 30, 2024

(54) COMBINATION OF MICHELIOLIDE DERIVATIVES OR NANOPARTICLES WITH IONIZING RADIATION AND CHECKPOINT INHIBITORS FOR CANCER THERAPY

(71) Applicant: The University of Chicago, Chicago, IL (US)

(72) Inventors: Wenbin Lin, Chicago, IL (US); Christina Chan, Chicago, IL (US); Wenbo Han, Chicago, IL (US)

(73) Assignee: The University of Chicago, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/855,327

(22) Filed: Jun. 30, 2022

(65) Prior Publication Data

US 2023/0036839 A1  Feb. 2, 2023

Related U.S. Application Data

(60) Continuation of application No. 16/859,594, filed on Apr. 27, 2020, now Pat. No. 11,389,422, which is a division of application No. 16/381,774, filed on Apr. 11, 2019, now abandoned.

(60) Provisional application No. 62/657,112, filed on Apr. 13, 2018.

(51) Int. Cl.

| | |
|---|---|
| *A61K 31/343* | (2006.01) |
| *A61K 45/06* | (2006.01) |
| *A61K 47/68* | (2017.01) |
| *A61N 5/10* | (2006.01) |
| *A61P 35/00* | (2006.01) |
| *A61P 37/00* | (2006.01) |

(52) U.S. Cl.
CPC ............ *A61K 31/343* (2013.01); *A61K 45/06* (2013.01); *A61K 47/6803* (2017.08); *A61P 35/00* (2018.01); *A61P 37/00* (2018.01); *A61N 5/10* (2013.01)

(58) Field of Classification Search
CPC .. A61K 31/343; A61K 47/6803; A61K 45/06; A61P 37/00; A61P 35/00; A61N 5/10
See application file for complete search history.

(56) References Cited

U.S. PATENT DOCUMENTS

| | | | |
|---|---|---|---|
| 5,858,784 A | 1/1999 | Debs et al. | |
| 6,013,638 A | 1/2000 | Crystal et al. | |
| 6,022,737 A | 2/2000 | Niven et al. | |
| 6,136,295 A | 10/2000 | Edwards et al. | |
| 8,088,803 B2 | 1/2012 | Combs et al. | |
| 9,255,078 B2 | 2/2016 | Chen et al. | |
| 9,693,957 B2 | 7/2017 | Lin et al. | |
| 10,206,871 B2 | 2/2019 | Lin et al. | |
| 11,389,422 B2 | 7/2022 | Lin et al. | |
| 2003/0194803 A1 | 10/2003 | Mellor et al. | |
| 2004/0234623 A1 | 11/2004 | Munn et al. | |
| 2006/0258719 A1 | 11/2006 | Combs et al. | |
| 2007/0185165 A1 | 8/2007 | Combs et al. | |
| 2011/0135571 A1 | 6/2011 | Lin et al. | |
| 2014/0234210 A1 | 8/2014 | Lin et al. | |
| 2016/0279187 A1 | 9/2016 | Hoffmann | |
| 2016/0346204 A1 | 12/2016 | Lin et al. | |
| 2016/0367525 A1* | 12/2016 | Chen | A61K 31/4525 |
| 2017/0129911 A1 | 5/2017 | Lippard et al. | |
| 2017/0231903 A1 | 8/2017 | Lin et al. | |
| 2018/0153796 A1 | 6/2018 | Lin et al. | |
| 2019/0209460 A1 | 7/2019 | Lin et al. | |
| 2019/0314324 A1 | 10/2019 | Lin et al. | |
| 2020/0261403 A1 | 8/2020 | Lin et al. | |
| 2020/0277270 A1 | 9/2020 | Fasan et al. | |

FOREIGN PATENT DOCUMENTS

| | | |
|---|---|---|
| CN | 104876899 A | 9/2015 |
| WO | WO 99/29310 | 6/1999 |
| WO | WO 03/087347 | 10/2003 |
| WO | WO 2004/094409 | 11/2004 |
| WO | WO 2011/131103 A1 | 10/2011 |
| WO | WO 2013/009701 | 1/2013 |
| WO | WO 2015/069926 | 5/2015 |
| WO | WO 2017/028163 A1 | 2/2017 |
| WO | WO 2017/201528 | 11/2017 |
| WO | WO 2019/028250 | 2/2019 |
| WO | WO 2019/040335 A1 | 2/2019 |

OTHER PUBLICATIONS

Advisory Action corresponding to U.S. Appl. No. 16/859,594 dated Jun. 18, 2021.
Castañeda-Acosta et al., "Biomimetic Transformations of Parthenolide," J. Nat. Prod., 56(1), 90-98 (1993).
Guzman et al. "An orally bioavailable parthenolide analog selectively eradicates acute myelogenous leukemia stem and progenitor cells," Blood, 110, 4427-4435 (2007).
Li et al. "Dimethylaminomicheliolide Sensitizes Cancer Cells to Radiotherapy for Synergistic Combination with Immune Checkpoint Blockade" and Supporting Information, Advanced Therapeutics, 2100160, pp. 1-15 (2021).

(Continued)

*Primary Examiner* — Robert A Wax
*Assistant Examiner* — Olga V. Tcherkasskaya
(74) *Attorney, Agent, or Firm* — Jenkins, Taylor & Hunt, P.A.

(57) ABSTRACT

Nanoparticles comprising micheliolide (MCL) or derivatives thereof, and optionally additional therapeutic agents, such as chemotherapeutic agents, are described. Also described are methods of treating diseases, such as cancer, comprising the use of combinations of MCL or a derivative thereof with X-ray irradiation and/or other therapeutic agents, such as immune checkpoint inhibitors. The use of the combinations can provide synergistic anticancer therapeutic efficacy, for example, as the MCL or derivative thereof can both sensitize cancer cells to therapy and target resistant cancer stem cells (CSCs) for selective cell death.

16 Claims, 4 Drawing Sheets

(56) References Cited

OTHER PUBLICATIONS

Notice of Allowance corresponding to U.S. Appl. No. 16/859,594 dated Mar. 18, 2022.
Office Action (Restriction Requirement) corresponding to U.S. Appl. No. 16/381,774 dated Nov. 18, 2019.
Office Action corresponding to U.S. Appl. No. 16/381,774 dated Jan. 27, 2020.
Office Action corresponding to U.S. Appl. No. 16/859,594 dated Oct. 21, 2020.
Office Action corresponding to U.S. Appl. No. 16/859,594 dated Feb. 26, 2021.
Office Action corresponding to U.S. Appl. No. 16/859,594 dated Jul. 21, 2021.
Interview Summary corresponding to U.S. Appl. No. 16/859,594 dated Oct. 14, 2021.
Sun et al., "The radiosensitization effect of parthenolide in prostate cancer cells is mediated by nuclear factor-kappaB inhibition and enhanced by the presence of PTEN," Mol Cancer Ther., 6, 2477-2486 (2007).
Zhang et al., "Guaianolide Sesquiterpene Lactones, a Source to Discover Agents That Selectively Inhibit Acute Myelogenous Leukemia Stem and Progenitor Cells," J. Med. Chem., 55, 8757-8769 (2012).
Zunino et al., "Parthenolide induces significant apoptosis and production of reactive oxygen species in high-risk pre-B leukemia cells," Cancer Lett., 254, 119-127 (2007).

* cited by examiner

COMBINATION OF MICHELIOLIDE DERIVATIVES OR NANOPARTICLES WITH IONIZING RADIATION AND CHECKPOINT INHIBITORS FOR CANCER THERAPY

RELATED APPLICATIONS

This application is a continuation of U.S. patent application Ser. No. 16/859,594, filed on Apr. 27, 2020, which is a divisional of U.S. patent application Ser. No. 16/381,774, filed on Apr. 11, 2019, which claims the benefit of U.S. Provisional Patent Application Ser. No. 62/657,112, filed Apr. 13, 2018, the disclosures of each of which are incorporated herein by reference in their entireties.

STATEMENT OF GOVERNMENT SUPPORT

This invention was made with government support under Grant No. U01-CA198989 awarded by the National Institutes of Health. The government has certain rights in the invention.

TECHNICAL FIELD

The presently disclosed subject matter relates to nanoparticles (NPs) comprising micheliolide (MCL) or a derivative thereof, as well as to the use of combinations of MCL or a derivative and/or NPs thereof in combination with X-ray irradiation and/or other therapeutic agents, e.g., immune checkpoint inhibitors, for treating disease. In some embodiments, the combinations can provide synergistic anticancer therapeutic efficacy.

| ABBREVIATIONS | |
|---|---|
| ° C. = | degrees Celsius |
| % = | percentage |
| µg = | microgram |
| µM = | micromolar |
| cm = | centimeter |
| CSCs = | cancer stem cells |
| DLS = | dynamic light scattering |
| DOPC = | 1,2-dioleoyl-sn-glycero-3-phosphocholine |
| DSPE—PEG$_{2k}$ = | 1,2-distearoyl-sn-glycero-3-phosphoethanolamine-N-[amino(polyethylene glycol)2000] |
| DMAMCL = | dimethylamino micheliolide |
| ESI-MS = | electrospray ionization mass spectrometry |
| EtOH = | ethanol |
| Gy = | gray |
| Kg = | kilogram |
| kVp = | peak kilovoltage |
| mA = | milliampere |
| MCL = | micheliolide |
| mg = | milligram |
| mL | milliliter |
| mm = | millimeter |
| mmol = | millimole |
| MOF = | metal-organic framework |
| NCP = | nanoscale coordination polymer |
| nm = | nanometer |
| nMOF = | nanoscale metal-organic framework |
| NMR = | nuclear magnetic resonance |
| NPs = | nanoparticles |
| Ox = | oxaliplatin |
| PD-L1 = | programmed death ligand 1 |
| PEG = | poly(ethylene glycol) |
| PBS = | phosphate buffered saline |
| SBU = | secondary building unit |
| THF = | tetrahydrofuran |

BACKGROUND

Chemotherapy and radiotherapy are among the powerful anticancer therapies used across a multitude of cancer types. However, the effective use of these therapies can be limited due to undesirable side effects to healthy cells at high dosages. In addition, these therapies are often compromised by the development of drug and radio-resistance by tumor cells.

Accordingly, there is an ongoing need for additional cancer treatment methods and compositions, such as those with enhanced anticancer efficacy. For instance, there is an ongoing need for additional cancer treatment methods and compositions that can be used to treat drug- and/or radio-resistant cancers and/or that can be used to treat cancer while avoiding the development of drug- and/or radio-resistant cancer cells.

SUMMARY

In some embodiments, the presently disclosed subject matter provides a composition comprising a nanoparticle and micheliolide (MCL) or a derivative thereof. In some embodiments, the composition comprises a derivative of MCL, wherein said derivative is dimethylamino micheliolide (DMAMCL) or a lipid conjugate of MCL.

In some embodiments, the MCL or the derivative thereof is attached to or sequestered within the nanoparticle. In some embodiments, the nanoparticle is selected from the group comprising a polymeric micelle, a liposome, a dendrimer, an organic polymer-based nanoparticle, a silica-based nanoparticle, a nanoscale coordination polymer, a nanoscale metal-organic framework, and an inorganic nanoparticle.

In some embodiments, the nanoparticle comprises a core and one or more coating layers or agents covering at least a portion of an outer surface of the core. In some embodiments, the core comprises an organic polymer, a silica-based material, a nanoscale coordination polymer, a metal-organic framework, or an inorganic material. In some embodiments, the one or more coating agents or layers are selected from a metal oxide, a polymer, a single lipid layer, a lipid bilayer, and combinations thereof. In some embodiments, the one or more coating agents or layers further comprise a passivating agent, a targeting agent, and/or an imaging agent.

In some embodiments, the MCL or derivative thereof is attached to or sequestered in the nanoparticle core. In some embodiments, the MCL or the derivative thereof is attached to or sequestered in a nanoparticle coating layer.

In some embodiments, the composition further comprises a chemotherapeutic agent and/or an immunotherapy agent. In some embodiments, the chemotherapeutic agent is attached or sequestered in a nanoparticle core or a nanoparticle coating layer. In some embodiments, the chemotherapeutic agent is selected from the group comprising cisplatin, oxaliplatin, or prodrugs thereof; doxorubicin, daunorubicin, docetaxel, mitoxanthrone, paclitaxel, digitoxin, gemcitabine, methotrexate, leucovorin, pemetresed disodium, vinblastine, vincristine, vindesine, cytarabine, azathioprine, melphalan, imitinib, anastrozole, letrozole, carboplatin, etoposide, vinorelbine, and septacidin. In some embodiments, the immunotherapy agent is selected from the group comprising an anti-CD52 antibody, an anti-CD20 antibody, anti-CD47 antibody, an anti-GD2 antibody, polysaccharide K, a cytokine, Alemtuzumab, Ofatumumab, Rituximab, Zevalin, Adcetris, Kadcyla, Ontak, a PD-1 inhibitor, a PD-L1 inhibitor, a CTLA-4 inhibitor, an IDO inhibitor, a CCR7 inhibitor, an OX40 inhibitor, a TIM3 inhibitor, and a LAG3 inhibitor. In some embodiments, the immunotherapy agent is attached to or sequestered in a nanoparticle coating layer.

In some embodiments, the presently disclosed subject matter provides a pharmaceutical composition comprising a composition comprising a nanoparticle and micheliolide (MCL) or a derivative thereof and a pharmaceutically acceptable carrier.

In some embodiments, the presently disclosed subject matter provides a method for treating a disease in a subject in need thereof, the method comprising: administering to the subject micheliolide (MCL) or a derivative thereof; and exposing at least a portion of the subject to ionizing irradiation energy. In some embodiments, administering the MCL or derivative thereof comprises administering a nanoparticle and/or a nanoscale coordination polymer (NCP) comprising the MCL or derivative thereof. In some embodiments, the ionizing irradiation energy is X-rays or protons.

In some embodiments, the disease is cancer. In some embodiments, the disease is selected from the group comprising a skin cancer, a connective tissue cancer, an adipose cancer, a breast cancer, a head and neck cancer, a lung cancer, a stomach cancer, a pancreatic cancer, an ovarian cancer, a cervical cancer, a uterine cancer, an anogenital cancer, a kidney cancer, a bladder cancer, a colon cancer, a prostate cancer, a central nervous system (CNS) cancer, a retinal cancer, a blood cancer, a neuroblastoma, multiple myeloma, and a lymphoid cancer.

In some embodiments, the method further comprises administering to the subject an additional therapeutic agent or treatment selected from an immunotherapy agent and/or a cancer treatment, wherein the cancer treatment is selected from the group comprising surgery, chemotherapy, toxin therapy, cryotherapy and gene therapy. In some embodiments, the additional therapeutic agent or treatment comprises an immunotherapy agent. In some embodiments, the immunotherapy agent is an immune checkpoint inhibitor. In some embodiments, the immune checkpoint inhibitor is selected from the group comprising a PD-1 inhibitor, a PD-L1 inhibitor, a CTLA-4 inhibitor, an IDO inhibitor, a CCR7 inhibitor, an OX40 inhibitor, a TIM3 inhibitor, and a LAG3 inhibitor.

In some embodiments, the presently disclosed subject matter provides a method for treating a disease in a subject in need thereof, the method comprising: administering to the subject micheliolide (MCL) or a derivative thereof; and administering to the subject one or more additional therapeutic agent or treatment. In some embodiments, administering to the subject MCL or a derivative thereof comprises administering to the subject a nanoparticle comprising MCL or a derivative thereof. In some embodiments, the one or more additional therapeutic agent or treatment agent is selected from a chemotherapeutic agent, an immune therapy agent, radiotherapy, surgery, chemotherapy, toxin therapy, cryotherapy and gene therapy.

In some embodiments, the disease is cancer. In some embodiments, the disease is selected from the group comprising a skin cancer, a connective tissue cancer, an adipose cancer, a breast cancer, a head and neck cancer, a lung cancer, a stomach cancer, a pancreatic cancer, an ovarian cancer, a cervical cancer, a uterine cancer, an anogenital cancer, a kidney cancer, a bladder cancer, a colon cancer, a prostate cancer, a central nervous system (CNS) cancer, a retinal cancer, a blood cancer, a neuroblastoma, multiple myeloma, and a lymphoid cancer.

In some embodiments, the one or more additional therapeutic agent or treatment comprises an immunotherapeutic agent. In some embodiments, the immunotherapeutic agent is an immune checkpoint inhibitor.

In some embodiments, the one or more additional therapeutic agent or treatment further comprises radiotherapy. In some embodiments, the one or more additional therapeutic agent or treatment agent further comprises one or more of surgery, toxin therapy, cryotherapy and gene therapy. In some embodiments, the one or more additional treatment agent comprises chemotherapy.

Accordingly, it is an object of the presently disclosed subject matter to provide compositions comprising MCL or a derivative thereof in a nanoparticle and/or in combination with another therapeutic agent, e.g., a chemotherapeutic agent or an immunotherapeutic agent, as well as methods of treating disease using the compositions, alone or in combination with X-ray irradiation and/or another therapy, e.g., immunotherapy.

These and other objects are achieved in whole or in part in the presently disclosed subject matter. An object of the presently disclosed subject matter having been stated above, other objects and advantages will become apparent upon a review of the following descriptions, examples, and figures.

DETAILED DESCRIPTION

Figure 1:
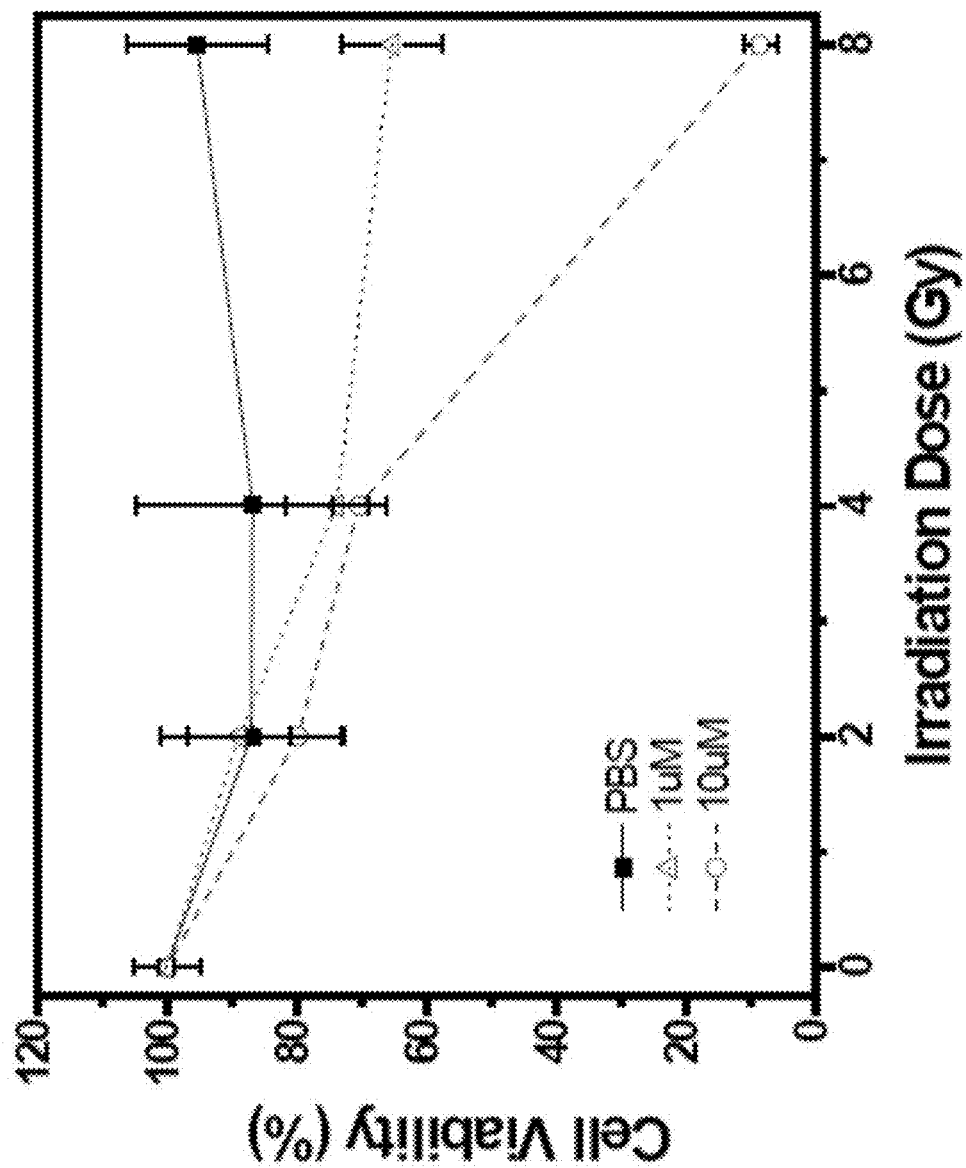
FIG. 1 is a graph showing the in vitro cytotoxicity of combinations of dimethylamino micheliolide (DMAMCL) and irradiation in mouse glioma 261 (GL261) cells. The cytotoxic effect of the combination is represented by a decrease in cell viability (in percentage (5%)). The cytotoxicity was measured at two different concentrations of DMAMCL: 1 micromolar (1 µM, open triangles) and 10 µM (open circles). The irradiation dose varied from 0 gray (Gy) to 8 Gy as indicated on the x-axis. For comparison, cell viability data for GL261 cells treated with irradiation and phosphate buffered saline (PBS, filled squares) in place of the DMAMCL is also shown.

The presently disclosed subject matter will now be described more fully hereinafter with reference to the accompanying Examples, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

Unless otherwise defined, all technical and scientific terms used herein have the same meaning as commonly understood by one of ordinary skill in the art to which this presently described subject matter belongs. Although any methods, devices, and materials similar or equivalent to those described herein can be used in the practice or testing of the presently disclosed subject matter, representative methods, devices, and materials are now described. All publications, patent applications, patents, and other references mentioned herein are incorporated by reference in their entirety.

Throughout the specification and claims, a given chemical formula or name shall encompass all optical and stereoisomers, as well as racemic mixtures where such isomers and mixtures exist.

I. Definitions

While the following terms are believed to be well understood by one of ordinary skill in the art, the following definitions are set forth to facilitate explanation of the presently disclosed subject matter.

Following long-standing patent law convention, the terms "a", "an", and "the" refer to "one or more" when used in this application, including the claims. Thus, for example, reference to "a chemotherapeutic agent" includes a plurality of such chemotherapeutic agents, and so forth.

Unless otherwise indicated, all numbers expressing quantities of size, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about", when referring to a value or to an amount of size (i.e., diameter), dose, weight, concentration, or percentage is meant to encompass variations of in one example ±20% or ±10%, in another example ±5%, in another example ±1%, and in still another example ±0.1% from the specified amount, as such variations are appropriate to perform the disclosed methods.

Numerical ranges recited herein by endpoints include all numbers and fractions subsumed within that range (e.g. 1 to 5 includes, but is not limited to, 1, 1.5, 2, 2.75, 3, 3.90, 4, and 5).

As used herein, the term "and/or" when used in the context of a listing of entities, refers to the entities being present singly or in combination. Thus, for example, the phrase "A, B, C, and/or D" includes A, B, C, and D individually, but also includes any and all combinations and sub-combinations of A, B, C, and D.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" can mean at least a second or more.

The term "comprising", which is synonymous with "including," "containing," or "characterized by" is inclusive or open-ended and does not exclude additional, unrecited elements or method steps. "Comprising" is a term of art used in claim language which means that the named elements are present, but other elements can be added and still form a construct or method within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

As used herein the term "alkyl" can refer to $C_1$-20 inclusive, linear (i.e., "straight-chain"), branched, or cyclic, saturated or at least partially and in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_1$-8 alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_1$-8 straight-chain alkyls. In other embodiments, "alkyl" refers, in particular, to $C_1$-8 branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. In some embodiments, there can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

"Alkylene" refers to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene ($-CH_2-$); ethylene ($-CH_2-CH_2-$); propylene ($-(CH_2)_3-$); cyclohexylene ($-C_6H_{10}-$); $-CH=CH-CH=CH-$; $-CH=CH-CH_2-$; $-(CH_2)_q-N(R)-(CH_2)_r-$, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl ($-O-CH_2-O-$); and ethylenedioxyl ($-O-(CH_2)_2-O-$). An alkylene group can have about 2 to about 3 carbon atoms and can further have 6-20 carbons.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and $-NR'R''$, wherein R' and R'' can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

The term "arylene" refers to a bivalent aromatic group, e.g., a bivalent phenyl or naphthyl group. The arylene group can optionally be substituted with one or more aryl group substituents and/or include one or more heteroatoms. The term "arylene" includes bivalent groups comprising more than one aromatic ring fused to or linked to one another (e.g., via a covalent bond or a linking group), such as bivalent biphenyl or bivalent terphenyl.

The term "aralkyl" as used herein refers to a -alkyl-aryl group, which can be substituted or unsubstituted. An exemplary aralkyl group is benzyl.

The term "acyl" refers to the group $-C(=O)R$, wherein R is a substituted or unsubstituted alkyl, aralkyl, or aryl group.

The term "amino" refers to the group $-N(R)_2$ wherein each R is independently H, alkyl, substituted alkyl, aryl, substituted aryl, aralkyl, or substituted aralkyl. The terms "aminoalkyl" and "alkylamino" can refer to the group $-N(R)_2$ wherein each R is H, alkyl or substituted alkyl, and wherein at least one R is alkyl or substituted alkyl. "Arylamine" and "aminoaryl" refer to the group $-N(R)_2$ wherein each R is H, aryl, or substituted aryl, and wherein at least one R is aryl or substituted aryl, e.g., aniline (i.e., $-NHC_6H_5$).

The term "lipid" can refer to a hydrophobic or amphiphilic small molecule, such as, but not limited to a fatty acid, a sterol, a fat-soluble vitamin, a phospholipid, a glycerolipid, a glycerophospholipid, a sphingolipid, a saccharolipid, or a polyketide.

As used herein, the term "metal-organic framework" or "MOF" refers to a solid two- or three-dimensional network comprising both metal and organic components, wherein the organic components include at least one, and typically more than one carbon atom. In some embodiments, the material is crystalline. In some embodiments, the material is amorphous. In some embodiments, the material is porous. In some embodiments, the metal-organic matrix material is a coordination polymer, which comprises repeating units of coordination complexes comprising a metal-based secondary building unit (SBU), such as a metal ion or metal complex, and a bridging polydentate (e.g., bidentate or tridentate) organic ligand. In some embodiments, the material contains more than one type of SBU or metal ion. In some embodiments, the material can contain more than one type of organic bridging ligand.

The term "nanoscale metal-organic framework" can refer to a nanoscale particle comprising an MOF.

The terms "nanoscale particle," nanomaterial," and "nanoparticle" refer to a structure having at least one region with a dimension (e.g., length, width, diameter, etc.) of less than about 1,000 nm. In some embodiments, the dimension is smaller (e.g., less than about 500 nm, less than about 250 nm, less than about 200 nm, less than about 150 nm, less than about 125 nm, less than about 100 nm, less than about 80 nm, less than about 70 nm, less than about 60 nm, less than about 50 nm, less than about 40 nm, less than about 30 nm or even less than about 20 nm). In some embodiments, the dimension is between about 20 nm and about 250 nm (e.g., about 20 nm, 30 nm, 40 nm, 50 nm, 60 nm, 70 nm, 80 nm, 90 nm, 100 nm, 110 nm, 120 nm, 130 nm, 140 nm, 150 nm, 160 nm, 170 nm, 180 nm, 190 nm, 200 nm, 210 nm, 220 nm, 230 nm, 240 nm, or 250 nm).

In some embodiments, the nanoparticle is approximately spherical. When the nanoparticle is approximately spherical, the characteristic dimension can correspond to the diameter of the sphere. In addition to spherical shapes, the nanomaterial can be disc-shaped, plate-shaped (e.g., hexagonally plate-like), oblong, polyhedral, rod-shaped, cubic, or irregularly-shaped.

The nanoparticle can comprise a core region (i.e., the space between the outer dimensions of the particle) and an outer surface (i.e., the surface that defines the outer dimensions of the particle). In some embodiments, the nanoparticle can have one or more coating layers surrounding or partially surrounding the nanoparticle core. Thus, for example, a spherical nanoparticle can have one or more concentric coating layers, each successive layer being dispersed over the outer surface of a layer closer to the center of the particle.

In some embodiments, the presently disclosed nanoparticle can comprise a solid metal-organic framework matrix, which can comprise one or more pores or hollow interior regions. The matrix can be amorphous or crystalline. In some embodiments, the nanoparticle core can further comprise one or more of: MCL or a derivative thereof; an optical imaging agent; and/or another therapeutic agent (e.g., an anticancer agent or an immunotherapeutic agent), which can be physically trapped within the matrix, coordinated to a metal ion of the matrix, or chemically bonded (e.g., to an organic bridging ligand in the matrix) via a covalent or ionic bond. In some embodiments, a chemotherapeutic agent or prodrug thereof can be an organic bridging ligand within a metal-organic matrix material that forms the core of the nanoparticle. For example, when the matrix material is a metal bisphosphonate coordination polymer, the bisphosphonate can be a chemotherapeutic agent or prodrug thereof.

When the core comprises a non-matrix therapeutic and/or imaging agent, said agents can be said to be "embedded" in the nanoparticle. "Embedded" can refer to a therapeutic agent or an imaging agent that is bound, for example covalently bound or bound via a coordinative bond, inside the core of the particle (e.g., to a bisphosphonate, dicarboxylate, or metal ion of the matrix material). Alternatively, the complex or agent can be "sequestered" (i.e., non-covalently/physically encapsulated) inside pores in the core or interact with a core material via hydrogen bonding, London dispersion forces, or any other non-covalent interaction.

The terms "polymer" and "polymeric" refer to chemical structures that have repeating units (i.e., multiple copies of a given chemical substructure). Polymers can be formed from polymerizable monomers. A polymerizable monomer is a molecule that comprises one or more moieties that can react to form bonds (e.g., covalent or coordination bonds) with moieties on other molecules of polymerizable monomer. Generally, each polymerizable monomer molecule can bond to two or more other molecules. In some cases, a polymerizable monomer will bond to only one other molecule, forming a terminus of the polymeric material.

Polymers can be organic, or inorganic, or a combination thereof. As used herein, the term "inorganic" refers to a compound or composition that contains at least some atoms other than carbon, hydrogen, nitrogen, oxygen, sulfur, phosphorous, or one of the halides. Thus, for example, an inorganic compound or composition can contain one or more silicon atoms and/or one or more metal atoms.

As used herein "organic polymers" are those that do not include silica or metal atoms in their repeating units. Exemplary organic polymers include polyvinylpyrrolidone (PVO), polyesters, polyamides, polyethers, polydienes, and the like. Some organic polymers contain biodegradable linkages, such as esters or amides, such that they can degrade over time under biological conditions.

The term "hydrophilic polymer" as used herein generally refers to hydrophilic organic polymers, such as but not limited to, polyvinylpyrrolidone, polyvinylmethylether, polymethyloxazoline, polyethyloxazoline, polyhydroxypropyloxazoline, polyhydroxypropylmethacrylamide, polymethyacrylamide, polydimethylacrylamide, polyhydroxylpropylmethacrylate, polyhydroxyethylacrylate, hydroxymethylcellulose, hydroxyethylcellulose, polyethylenimine (PEI), polyethyleneglycol (i.e., PEG) or another hydrophilic poly(alkyleneoxide), polyglycerine, and polyaspartamide. The term "hydrophilic" refers to the ability of a molecule or chemical species to interact with water. Thus, hydrophilic polymers are typically polar or have groups that can hydrogen bond to water.

The terms "bonding" or "bonded" and variations thereof can refer to either covalent or non-covalent bonding. In some cases, the term "bonding" refers to bonding via a coordinate bond. The term "conjugation" can refer to a bonding process, as well, such as the formation of a covalent linkage or a coordinate bond.

A "coordination complex" is a compound in which there is a coordinate bond between a metal ion and an electron pair donor, ligand or chelating group. Thus, ligands or chelating groups are generally electron pair donors, molecules or molecular ions having unshared electron pairs available for donation to a metal ion.

The term "coordinate bond" refers to an interaction between an electron pair donor and a coordination site on a metal ion resulting in an attractive force between the electron pair donor and the metal ion. The use of this term is not intended to be limiting, in so much as certain coordinate bonds also can be classified as having more or less covalent character (if not entirely covalent character) depending on the characteristics of the metal ion and the electron pair donor.

As used herein, the term "ligand" refers generally to a species, such as a molecule or ion, which interacts, e.g., binds, in some way with another species. More particularly, as used herein, a "ligand" can refer to a molecule or ion that binds a metal ion in solution to form a "coordination complex." See Martell, A. E., and Hancock, R. D., *Metal Complexes in Aqueous Solutions*, Plenum: New York (1996), which is incorporated herein by reference in its entirety. The terms "ligand" and "chelating group" can be used interchangeably. The term "bridging ligand" can refer to a group that bonds to more than one metal ion or complex, thus providing a "bridge" between the metal ions or complexes. Organic bridging ligands can have two or more groups with unshared electron pairs separated by, for example, an alkylene or arylene group. Groups with unshared electron pairs, include, but are not limited to, —$CO_2H$, —$NO_2$, amino, hydroxyl, thio, thioalkyl, —$B(OH)_2$, —$SO_3H$, $PO_3H$, phosphonate, and heteroatoms (e.g., nitrogen, oxygen, or sulfur) in heterocycles.

The term "coordination site" when used herein with regard to a ligand, e.g., a bridging ligand, refers to an unshared electron pair, a negative charge, or atoms or functional groups cable of forming an unshared electron pair or negative charge (e.g., via deprotonation under at a particular pH).

The term "imaging agent" refers to a chemical moiety that aids in the visualization of a sample. For example, an imaging agent can be a "contrast agent" and can refer to a moiety (a specific part of or an entire molecule, macromolecule, coordination complex, or nanoparticle) that increases the contrast of a biological tissue or structure being examined. The contrast agent can increase the contrast of a structure being examined using, for example, magnetic resonance imaging (MRI), optical imaging, positron emission tomography (PET) imaging, single photon emission computed tomography (SPECT) imaging, or a combination thereof (i.e., the contrast agent can be multimodal).

The term "MRI contrast agent" refers to a moiety that effects a change in induced relaxation rates of water protons in a sample.

The terms "optical imaging agent" or "optical contrast agent" refer to a group that can be detected based upon an ability to absorb, reflect or emit light (e.g., ultraviolet, visible, or infrared light). Optical imaging agents can be detected based on a change in amount of absorbance, reflectance, or fluorescence, or a change in the number of absorbance peaks or their wavelength maxima. Thus, optical imaging agents include those which can be detected based on fluorescence or luminescence, including organic and inorganic dyes.

The terms "fluorophore" and "fluorescent moiety" refer to species that can be excited by visible light or non-visible light (e.g., UV light). Examples of fluorophores include, but are not limited to: quantum dots and doped quantum dots (e.g., a semiconducting CdSe quantum dot or a Mn-doped CdSe quantum dot), fluorescein, fluorescein derivatives and analogues, indocyanine green, rhodamine, triphenylmethines, polymethines, cyanines, phalocyanines, naphthocyanines, merocyanines, lanthanide complexes or cryptates, fullerenes, oxatellurazoles, LaJolla blue, porphyrins and porphyrin analogues and natural chromophores/fluorophores such as chlorophyll, carotenoids, flavonoids, bilins, phytochrome, phycobilins, phycoerythrin, phycocyanines, retinoic acid and analogues such as retinoins and retinates.

The term "cancer" as used herein refers to diseases caused by uncontrolled cell division and/or the ability of cells to metastasize, or to establish new growth in additional sites. The terms "malignant", "malignancy", "neoplasm", "tumor," "cancer" and variations thereof refer to cancerous cells or groups of cancerous cells.

Particular types of cancer include, but are not limited to, skin cancers (e.g., melanoma), connective tissue cancers (e.g., sarcomas), adipose cancers, breast cancers, head and neck cancers, lung cancers (e.g., mesothelioma), stomach cancers, pancreatic cancers, ovarian cancers, cervical cancers, uterine cancers, anogenital cancers (e.g., testicular cancer), kidney cancers, bladder cancers, colon cancers, prostate cancers, central nervous system (CNS) cancers, retinal cancer, blood, neuroblastomas, multiple myeloma, and lymphoid cancers (e.g., Hodgkin's and non-Hodgkin's lymphomas).

The term "metastatic cancer" refers to cancer that has spread from its initial site (i.e., the primary site) in a patient's body.

The terms "anticancer drug", "chemotherapeutic", and "anticancer prodrug" refer to drugs (i.e., chemical compounds) or prodrugs known to, or suspected of being able to treat a cancer (i.e., to kill cancer cells, prohibit proliferation of cancer cells, or treat a symptom related to cancer). In some embodiments, the term "chemotherapeutic" as used herein refers to a non-MCL-based molecule that is used to treat cancer and/or that has cytotoxic ability. Some traditional or conventional chemotherapeutic agents can be described by mechanism of action or by chemical compound class, and can include, but are not limited to, alkylating agents (e.g., melphalan), anthracyclines (e.g., doxorubicin), cytoskeletal disruptors (e.g., paclitaxel), epothilones, histone deacetylase inhibitors (e.g., vorinostat), inhibitors of topoisomerase I or II (e.g., irinotecan or etoposide), kinase inhibitors (e.g., bortezomib), nucleotide analogs or precursors thereof (e.g., methotrexate), peptide antibiotics (e.g., bleomycin), platinum based agents (e.g., cisplatin or oxaliplatin), retinoids (e.g., tretinoin), and vinka alkaloids (e.g., vinblastine).

II. General Considerations

Water-soluble micheliolide (MCL) is a derivative of a natural sesquiterpene lactone, compounds commonly used to treat inflammation. The presently disclosed subject matter is related to the finding that MCL and related compounds can synergize with other disease treatments, particularly cancer treatments, such as chemotherapy and radiotherapy. Without being bound by any one theory, it is believed that the synergistic effects with regard to treating cancer can be related to the activity of the MCL or a related compound in sensitizing cancer cells to therapy and/or targeting resistant CSCs for selective cell death. In some embodiments, the combined efficacy of MCL and related compounds with the other treatment (e.g., with radiation) can be further enhanced by immune checkpoint inhibitors. In some embodiments, nanoparticles (NPs) containing MCL or a derivative thereof, and optionally one or more additional therapeutic agents (e.g., chemotherapeutic agents and/or immunotherapy agents), can be used to enhance the bioavailability and relative tumor deposition of MCL, its derivative and/or other agents, allowing for lower total doses and less frequent dosing.

Accordingly, in some embodiments, the presently disclosed subject matter relates to the use of MCL NPs, as well as to combinations of MCL or a derivative thereof and/or NPs with X-ray irradiation and/or other therapeutic agents, e.g., immune checkpoint inhibitors, for treating disease (e.g., cancer). In some embodiments, the combinations can provide synergistic anticancer therapeutic efficacy.

III. Compositions

In some embodiments, the presently disclosed subject matter provides a composition comprising: (i) a nanoparticle and (ii) MCL or a derivative thereof. MCL has the following structure:

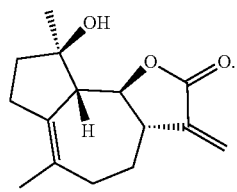

The cyclization of parthenolide, a sesquiterpene lactone found in feverfew (*Tanacetum parthenium*), to form MCL was described in 1993. See Castañeda-Acosta et al., J. Nat. Prod. 1993, 56(1), 90-98. Exemplary derivatives of MCL include, but are not limited to, the compounds described in U.S. Pat. No. 9,255,078, the disclosure of which is incorporated herein by reference in its entirety. For example, in some embodiments, the derivative of MCL comprises a compound wherein a carbon-carbon double bond has been replaced by a carbon-carbon single bond or a three-membered ring (e.g., an epoxide) and/or wherein one of the carbon atoms of the carbon-carbon double bond has been substituted, e.g., by a substituted or unsubstituted alkyl group; wherein an oxygen atom has been replaced by —CH$_2$— or a —NR'— group, wherein R' is an alkyl or substituted alkyl group; or wherein the hydroxyl group has been substituted by an alkyl, substituted alkyl, or acyl group. In some embodiments, the MCL derivative can be provided as a pharmaceutically acceptable salt. In some embodiments, the MCL derivative has a structure of the formula:

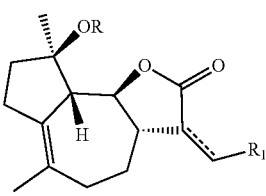

wherein ----- represents a single or double bond; R is selected from H, alkyl, substituted alkyl, and acyl; and $R_1$ is selected from H, alkyl, substituted alkyl, and amino; or a pharmaceutically acceptable salt thereof. In some embodiments, the amino group is —N($R_2$)($R_3$), wherein $R_2$ and $R_3$ are independently selected from H, alkyl (e.g., $C_{1-12}$ or $C_{1-6}$ alkyl), cycloalkyl, and substituted alkyl, or wherein $R_2$ and $R_3$ together form an alkylene group, e.g., propylene, butylene, or pentylene. In some embodiments, R is substituted alkyl, e.g., —$CH_2$—O—$R_4$, wherein $R_4$ is alkyl or alkenyl, optionally wherein $R_4$ is a lipid. In some embodiments, ----- represents a single bond and $R_1$ is —N($R_2$)($R_3$). In some embodiments, $R_2$ and $R_3$ are each methyl, ethyl or propyl. In some embodiments, the MCL derivative is a lipid conjugate of MCL or a derivative thereof, e.g., a compound wherein the hydroxyl group of MCL is covalently linked (e.g., via one or more ether or ester groups) to a lipid or lipid derivative (e.g., a sterol, a fatty acid or a fatty alcohol). In some embodiments, the MCL derivative is dimethylamino micheliolide (DMAMCL) or a lipid conjugate of MCL or DMAMCL.

Any suitable nanoparticle can be used, including but not limited to a polymeric micelle, a liposome, a dendrimer, an organic polymer-based nanoparticle, a silica-based nanoparticle, a nanoscale coordination polymer (NCP), a nanoscale metal-organic framework (nMOF), or an inorganic polymer, such as a gold or iron oxide nanoparticle. In some embodiments, the nanoparticle is a NCP and/or nMOF. Exemplary methods of preparing and using NCPs and nMOFs are described, for example in PCT International Patent Application Publication Nos. WO 2015/069926 and WO 2013/009701, U.S. Pat. No. 9,693,957, and U.S. Patent Application Publication No. 2016/0346204, the disclosures of each of which are incorporated herein by reference in their entireties.

In some embodiments, the nanoparticle comprises a nMOF that comprises metal-containing clusters or ions coordinated to organic molecules, wherein the material comprises repeating coordination units. The organic molecule (which can also be referred to as a "bridging ligand") can include, for example, carboxylate, phosphate, amino, mercapto, or hydroxyl groups to form coordinate bonds with a metal ion. The metal-containing clusters can be referred to as secondary building units (SBUs). In some embodiments, the SBUs are metal oxo clusters. For example, suitable SBUs can include, but are not limited to, Zr-oxo clusters, Hf-oxo clusters, Zn-oxo clusters, Ti-oxo clusters, Cu-carboxylate paddlewheels, and others. In some embodiments, the oxo clusters comprise anions selected from oxide ($O^{2-}$), hydroxide ($OH^-$), $S^{2-}$, $SH^-$, and formate ($HCO_2^-$). Each SBU is bonded to at least one other SBU via coordinative bonding to the same bridging ligand. Stated another way, each SBU is bonded via a coordinative bond to at least one bridging ligand, which is also coordinatively bonded to at least one other SBU.

Any suitable bridging ligand or ligands can be used. In some embodiments, each bridging ligand is an organic compound comprising multiple coordination sites. The coordination sites can each comprise a group capable of forming a coordinate bond with a metal cation or a group capable of forming such a group. Thus, each coordination site can comprise an unshared electron pair, a negative charge, or an atom or functional group capable of forming an unshared electron pair or negative charge. Typical coordination sites include, but are not limited to, functional groups such as carboxylate and derivatives there (e.g., esters, amides, anhydrides), nitrogen-containing groups (e.g., amines, nitrogen-containing aromatic and non-aromatic heterocycles), alcohols, phenols and other hydroxyl-substituted aromatic groups; ethers, acetylacetonate (i.e., —C(=O)$CH_2$C(=O)$CH_3$), phosphonates, phosphates, thiols, and the like. In some embodiments, each bridging ligand comprises between 2 and 10 coordination sites (i.e., 2, 3, 4, 5, 6, 7, 8, 9, or 10 coordination sites). In some embodiments, each bridging ligand is capable of binding to two or three SBUs. In some embodiments, each of the organic bridging ligands is a dicarboxylate or a tricarboxylate. The coordination sites of the organic bridging ligand can be bonded to the same polyvalent (e.g., divalent or trivalent) linking group, such as an alkylene or arylene group. In some embodiments, the bridging ligand further includes a group, such as an amino, hydroxyl, or thiol, that can form a covalent bond with a therapeutic agent (e.g., a chemotherapeutic or immunotherapeutic agent or MCL or a derivative thereof). For instance, the bridging ligand can be amino-triphenyldicarboxylic acid (amino-TPDC).

In some embodiments, the NCP is a metal bisphosphonate coordination polymer comprising a multivalent metal ion and a bisphosphonate. Any suitable multivalent metal ion can be used. In some embodiments, the multivalent metal ion is divalent. In some embodiments, the metal ion is $Ca^{2+}$, $Mg^{2+}$, $Mn^{2+}$, $Zn^{2+}$, or a combination thereof. In some embodiments, the metal is $Zn^{2+}$. In some embodiments, the bisphosphonate is a chemotherapeutic prodrug. Thus, in some embodiments, a chemotherapeutic is present as a bridging ligand between metal ions in the NCP. In some embodiments, the bisphosphonate is a cisplatin, oxaliplatin, or carboplatin prodrug. In some embodiments, the prodrug can be prepared by providing a metal complex based on cisplatin, oxaliplatin, carboplatin or another platinum coordination complex chemotherapeutic and having two hydroxyl ligands, and contacting the metal complex with diethoxyphosphinyl isocyanate, diethoxyphosphinyl isothiocyanate, diethoxyphosphinyl-containing carboxylic anhydride, or diethoxyphosphinyl-containing acyl chloride to form metal ligands that can provide phosphonate groups available for further coordinative bonding. Thus, in some embodiments, the bisphosphonate can be a bisphosphonate ester of cis, cis-trans-[Pt($NH_3$)$_2$$Cl_2$(OH)$_2$], a dihydroxyl complex based on cisplatin. Accordingly, in some embodiments, the bisphosphonate comprises a metal coordination complex and, therefore, includes a second metal ion, such as a Pt ion, in addition to the multivalent metal ion of the NCP.

Alternatively, in some embodiments, the bisphosphonate is an organic compound comprising at least two phosphonate groups and is free of an additional metal ion. For example, the bisphosphonate can have a structure of the formula:

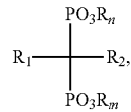

wherein n and m are each independently an integer between 0 and 2 (i.e., each independently 0, 1, or 2); each R is independently H, alkyl, substituted alkyl, aralkyl, aryl, or substituted aryl; $R_1$ is H, hydroxyl, halo, alkyl, substituted alkyl, amino, alkoxy, or alkylthio; and $R_2$ is halo, alkyl, substituted alkyl, aralkyl, substituted aralkyl, alkoxy, alkylthio, aryloxy, arylthio or arylamino; or an anion or salt thereof.

In some embodiments, the nanoparticle can comprise a core comprising one of the above-mentioned materials, such as an organic polymer, a silica-based matrix, a NCP, a nMOF, or an inorganic material, and further comprises one or more coating layers that surrounds at least a portion of the surface of the nanoparticle core and/or one or more coating agents, e.g., an agent attached to a coating layer or to the surface of the nanoparticle core. Suitable coating agents or layers include, but are not limited to, metal oxide, polymer (e.g., a silica-based polymer, such as silica, poly(siloxane), or poly(silsesquioxane), or an organic or hydrophilic organic polymer), a single lipid layer, a lipid bilayer, or a combination thereof. In some embodiments, one or more of the coating agents or layers can be derivatized with a targeting agent (such as a RGD peptide or an antibody or antibody fragment) and/or a passivating agent (such as a hydrophilic polymer e.g., poly(ethylene glycol) (PEG)) and or an imaging agent (such as a fluorescent moiety). In some embodiments, the one or more coating agents or layers are selected from the group comprising, but not limited to, dioleoyl L-α-phosphatidylethanolamine (DOPE), 1,2-dioleoyl-sn-glycero-3-phosphocholine (DOPC), 1,2-dioleoyl-sn-glycero-3-phosphate sodium salt (DOPA), 1,2-distearoyl-sn-glycero-3-phosphoethanolamine (DSPE), pegylated DSPE (e.g., DSPE-PEG$_{2k}$), 1,2-dioleoyl-3-trimethylammonium propane (DOTAP), anisamide-derivatized DOPE, cholesterol, silica, cRGfK-derivatized silica, PEG-derivatized silica, anisamide-PEG-derivatized silica, and combinations thereof.

In some embodiments, the MCL or derivative thereof is part of the nanoparticle. For example, in some embodiments, the MCL or its derivative can be attached to or sequestered within the nanoparticle core. For example, in some embodiments, the MCL derivative can include a chemical functional group that can form a covalent or ionic bond with an organic functional group or metal ion present in a component of an NCP or nMOF nanoparticle core. In some embodiments, the MCL or derivative thereof can be physically sequestered (e.g., encapsulated) in pores or channels in an NCP or nMOF nanoparticle core. In some embodiments, the MCL or its derivative can be attached (e.g., covalently or electrostatically) to a coating agent or layer or sequestered within a coating layer. In some embodiments, the MCL derivative can comprise a fatty acid or other lipid moiety and the MCL derivative can be sequestered in a lipid or lipid bilayer coating layer.

In some embodiments, the nanoparticle comprises a therapeutic agent other than the MCL or its derivative, e.g., a chemotherapeutic agent or an immunotherapy agent. Any suitable chemotherapeutic agent or immunotherapy agent can be used. In some embodiments, the chemotherapeutic agent can be selected from the group including, but not limited to, a platinum complex, such as cisplatin, oxaliplatin, carboplatin, or a prodrug thereof; doxorubicin; daunorubicin; docetaxel; mitoxanthrone; paclitaxel; digitoxin; gemcitabine; methotrexate; leucovorin; pemetresed disodium; vinblastine; vincristine; vindesine; cytarabine; azathioprine; melphalan; imitnib; anastrozole; letrozole; etoposide; vinorelbine; digoxin, and septacidin. In some embodiments, the nanoparticle can comprise more than one chemotherapeutic agent. In some embodiments, one or more chemotherapeutic agent is attached to or sequestered in a nanoparticle core. In some embodiments, one or more chemotherapeutic agent is attached to or sequestered in a nanoparticle coating layer.

In some embodiments, the immunotherapy agent is selected from the group including, but not limited to, an anti-CD52 antibody, an anti-CD20 antibody, an anti-CD20 antibody, anti-CD47 antibody an anti-GD2 antibody, a radiolabeled antibody, an antibody-drug conjugate, polysaccharide K, a neoantigen, an anti-LAG3 antibody, an anti-4-IBB antibody, an anti-TIM3 antibody and a cytokine. In some embodiments, the cytokine is an interferon, an interleukin, or tumor necrosis factor alpha (TNF-α). In some embodiments, the cytokine is selected from the group comprising IFN-α, INF-γ, IL-2, IL-12 and TNF-α. In some embodiments, the immunotherapy agent is selected from the group comprising Alemtuzumab, Ofatumumab, Rituximab, Zevalin, Adcetris, Kadcyla and Ontak. In some embodiments, the immunotherapy agent is selected from the group comprising a PD-1 inhibitor or a PD-L1 inhibitor, such as, but not limited to, BMS-936559 or BMS-936558 from Bristol-Myers Squibb, MPDL3280A from Genentech, MK-3475 from Merck, CT-011 from Curetech, and MED14736 from MedImmune; a CTLA-4 inhibitor (e.g., ipilimumab, tremelimumab); an indoleamine-2,3-dioxygenase (IDO) inhibitor; and a CCR7 inhibitor. The IDO inhibitor can be any suitable IDO inhibitor, such as, but not limited to oxadiazole and other heterocyclic IDO inhibitors, e.g., as reported in U.S. Patent Application Publication Nos. 2006/0258719 and 2007/0185165, which are incorporated herein by reference in their entireties. IDO inhibitors also include those described in PCT Publication WO 99/29310, incorporated herein by reference in its entirety, which reports methods for altering T cell-mediated immunity comprising altering local extracellular concentrations of tryptophan and tryptophan metabolites, BMS-986205 from Bristol-Myers Squibb or F001287 from Flexus, epacadostat from Incyte Corp., indoximod, IO-102, EOS-200271, HTI-1090, IO-101, KHK-2455, 1-methyl-DL-tryptophan, p-(3-benzofuranyl)-DL-alanine, p-[3-benzo(b)thienyl]-DL-alanine, and 6-nitro-L-tryptophan), and IDO inhibitors described in WO 03/087347, incorporated herein by reference in its entirety, also published as European Patent 1501918, which describes methods of making antigen-presenting cells for enhancing or reducing T cell tolerance. Compounds having IDO inhibitory activity are further reported in WO 2004/094409, and in U.S. Patent Application Publication No. 2004/0234623, incorporated herein by reference in its entirety, and which is directed to methods of treating a subject with a cancer or an infection by the administration of an inhibitor of indoleamine-2,3-dioxygenase in combination with other therapeutic modalities. In some embodiments, the small molecule inhibitors are those disclosed in U.S. Pat. No. 8,088,803, which is incorporated by reference in its entirety herein. In some embodiments, the immunotherapy agent is an immune checkpoint inhibitor (e.g., an antibody immune checkpoint inhibitor, such as, but not limited to, a PD-1/PD-L1 antibody, a CTLA-4 antibody, an OX40 antibody, a TIM3 antibody, a LAG3 antibody, an anti-CD47 antibody). In some embodiments, one or more immunotherapy agent is attached to or sequestered in a nanoparticle core. In some embodiments, one or more immunotherapy agent is attached to or sequestered in a nanoparticle coating layer.

In some embodiments, the nanoparticle comprises both MCL or a derivative thereof and one or more additional therapeutic agents (e.g., chemotherapeutic and/or immunotherapy agents). The other therapeutic agent can be attached to or sequestered within the nanoparticle core or can be attached to or sequestered in a coating layer or agent. In some embodiments, the nanoparticle is an NCP or nMOF comprising a chemotherapeutic agent, e.g., cisplatin, oxaliplatin, or a prodrug thereof, and the nanoparticle further comprises a lipid coating layer comprising the MCL or its derivative, e.g., a MCL lipid conjugate. In some embodiments, both the MCL or its derivative and the additional therapeutic agent are attached to or sequestered in the nanoparticle core. In some embodiments, both the MCL or its derivative and the additional therapeutic agent are attached to or sequestered in a coating layer, attached to the nanoparticle core surface, or attached to a coating agent.

In some embodiments, the composition comprises a mixture of nanoparticles, wherein one type of nanoparticle comprises MCL or a derivative thereof and another type of nanoparticle comprises one or more additional therapeutic agents (e.g., a chemotherapeutic, an immunotherapeutic and/or a nucleic acid therapeutic agent).

IV. Pharmaceutical Compositions

In some embodiments, the presently disclosed subject matter provides a composition comprising MCL or a derivative and/or nanoparticle thereof as described herein and a pharmaceutically acceptable carrier, e.g., a pharmaceutically acceptable carrier that is pharmaceutically acceptable in humans. In some embodiments, the composition can also include other components, such as, but not limited to antioxidants, buffers, bacteriostatics, bactericidal antibiotics, suspending agents, thickening agents, and solutes that render the composition isotonic with the bodily fluids of a subject to whom the composition is to be administered.

For example, suitable formulations can include aqueous and non-aqueous sterile injection solutions that can contain anti-oxidants, buffers, bacteriostatics, bactericidal antibiotics, and solutes that render the formulation isotonic with the bodily fluids of the subject; and aqueous and non-aqueous sterile suspensions that can include suspending agents and thickening agents. The formulations can be presented in unit-dose or multi-dose containers, for example sealed ampoules and vials, and can be stored in a frozen or freeze-dried (lyophilized) condition requiring only the addition of sterile liquid carrier, for example water for injections, immediately prior to use. Some exemplary ingredients are sodium dodecyl sulfate (SDS), in one example in the range of 0.1 mg/ml to 10 mg/ml, in another example about 2.0 mg/ml; and/or mannitol or another sugar, for example in the range of 10 mg/ml to 100 mg/ml, in another example about 30 mg/ml; and/or phosphate-buffered saline (PBS).

It should be understood that in addition to the ingredients particularly mentioned above, the formulations of the presently disclosed subject matter can include other agents conventional in the art having regard to the type of formulation in question. For example, sterile pyrogen-free aqueous and non-aqueous solutions can be used.

The methods and compositions disclosed herein can be used on a sample either in vitro (for example, on isolated cells or tissues) or in vivo in a subject (i.e. living organism, such as a patient). In some embodiments, the subject is a human subject, although it is to be understood that the principles of the presently disclosed subject matter indicate that the presently disclosed subject matter is effective with respect to all vertebrate species, including mammals, which are intended to be included in the terms "subject" and "patient". Moreover, a mammal is understood to include any mammalian species for which employing the compositions and methods disclosed herein is desirable, particularly agricultural and domestic mammalian species.

As such, the methods of the presently disclosed subject matter are particularly useful in warm-blooded vertebrates. Thus, the presently disclosed subject matter concerns mammals and birds. More particularly provided are methods and compositions for mammals such as humans, as well as those mammals of importance due to being endangered (such as Siberian tigers), of economic importance (animals raised on farms for consumption by humans), and/or of social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), rodents (e.g., mice, rats, hamsters, gerbils, etc.) and horses. Also provided is the treatment of birds, including the treatment of those kinds of birds that are endangered, kept in zoos or as pets (e.g., parrots), as well as fowl, and more particularly domesticated fowl, for example, poultry, such as turkeys, chickens, ducks, geese, guinea fowl, and the like, as they are also of economic importance to humans. Thus, also provided is the treatment of livestock including, but not limited to domesticated swine (pigs and hogs), ruminants, horses, poultry, and the like.

Suitable methods for administration of a composition of the presently disclosed subject matter include, but are not limited to intravenous and intratumoral injection, oral administration, subcutaneous administration, intraperitoneal injection, intracranial injection, and rectal administration. Alternatively, a composition can be deposited at a site in need of treatment in any other manner, for example by spraying a composition within the pulmonary pathways. The particular mode of administering a composition of the presently disclosed subject matter depends on various factors, including the distribution and abundance of cells to be treated and mechanisms for metabolism or removal of the composition from its site of administration. For example, relatively superficial tumors can be injected intratumorally. By contrast, internal tumors can be treated following intravenous injection.

In one embodiment, the method of administration encompasses features for regionalized delivery or accumulation at the site to be treated. In some embodiments, a composition is delivered intratumorally. In some embodiments, selective delivery of a composition to a target is accomplished by intravenous injection of the composition followed by irradiation (e.g., X-ray irradiation) of the target.

For delivery of compositions to pulmonary pathways, compositions of the presently disclosed subject matter can be formulated as an aerosol or coarse spray. Methods for preparation and administration of aerosol or spray formulations can be found, for example, in U.S. Pat. Nos. 5,858,784; 6,013,638; 6,022,737; and 6,136,295.

In some embodiments, an effective dose of a composition of the presently disclosed subject matter is administered to a subject. An "effective amount" is an amount of the composition sufficient to produce detectable treatment (e.g., tumor size reduction, pain relief, reduction of the concentration of a disease-related blood marker, etc.). Actual dosage levels of constituents of the compositions of the presently disclosed subject matter can be varied so as to administer an amount of the composition that is effective to achieve the desired effect for a particular subject and/or target. The selected dosage level can depend upon the activity (e.g., nanoparticle drug loading and/or the $IC_{50}$ of the therapeutic components in certain cell types (e.g., cancer cell lines) of the composition and the route of administration.

After review of the disclosure herein of the presently disclosed subject matter, one of ordinary skill in the art can tailor the dosages to an individual subject, taking into account the particular formulation, method of administration to be used with the composition, and nature of the target to be treated. Such adjustments or variations, as well as evaluation of when and how to make such adjustments or variations, are well known to those of ordinary skill in the art.

A dose may be administered on an as needed basis or every hour, every 2 hours, every three hours, every four hours, every five hours, every six hours, every seven hours, every eight hours, every nine hours, every ten hours, every eleven hours, every 12 hours, every eighteen hours, or every 24 hours (or any range derivable therein) or 1 time per day, 2 times per day, 3 times per day, 4 times per day, 5 times per day, 6 times per day, 7 times per day, 8 times per day, or 9 times per day (or any range derivable therein). A dose can be first administered before or after symptoms are exhibited by the subject; after a clinician evaluates the subject for the disease; or before, at about the same time as, or after administration of a second treatment (chemotherapy, radiation therapy, immunotherapy). In some embodiments, the patient is administered a first dose of a compound, such as MCL, 1 hour, 2 hours, 3 hours, 4 hours, 5 hours, 6 hours, 7 hours, 8 hours, 9 hours, 10 hours, 11 hours, 12 hours (or any range derivable therein) or 1 day, 2 days, 3 days, 4 days, or 5 days after the subject exhibits signs or symptoms of the disease (or any range derivable therein). The subject can be treated for 1 day, 2 days, 3 days, 4 days, 5 days, 6 days, 7 days, 8 days, 9 days, 10 days or more days (or any range derivable therein) or until symptoms of an the disease, such as tumor size, have disappeared or been reduced or after 6 hours, 12 hours, 18 hours, or 24 hours or 1 day, 2 days, 3 days, 4 days, or 5 days after symptoms of the disease have disappeared or been reduced.

V. Methods of Treating Disease Using Combinations Comprising MCL or a Derivative Thereof and Another Therapeutic Agent and/or Radiation In some embodiments, the presently disclosed subject matter provides a method for treating a disease (e.g., cancer or another hyperproliferative disease) by using the MCL or derivative and/or nanoparticle thereof and/or pharmaceutical composition thereof in combination with another treatment modality, e.g., a chemotherapeutic, an immunotherapeutic, radiation, surgery, etc. In some embodiments, the other treatment modality is radiation. Thus, in some embodiments, the presently disclosed subject matter provides a method of treating a disease in a subject in need thereof, the method comprising: administering to the subject an MCL or derivative and/or nanoparticle thereof and/or pharmaceutical composition thereof as described herein; and irradiating at least a portion of the subject with ionizing radiation, such as with x-rays and/or protons. In some embodiments, the method comprises administering a nanoparticle and/or NCP comprising MCL or a derivative thereof. In some embodiments, the subject is a mammal. In some embodiments, the subject is a human.

In some embodiments, the patients are irradiated with a linear accelerator (LINAC), using conventional techniques, Intensity-Modulated Radiation Therapy (IMRT), Image Guided Radiation Therapy (IGRT), or Stereotactic Body Radio Therapy (SBRT), a $^{60}Co$ radiation source, an implanted radioactive seed such as the ones used in brachytherapy, an orthovoltage or supervoltage X-ray irradiator, a high energy electron beam generated from LINAC, or a proton source.

In some embodiments, the γ-rays generated by a LINAC pass through an energy modulator (filter) before irradiating the patient, optionally wherein the filter comprises one or more element(s) with atomic number(s) of at least 20, further optionally wherein the filter comprises copper. In some embodiments, the filter has a thickness that is less than 5 mm, less than 4 mm, less than 3 mm, less than 2 mm, less than 1 mm, less than 0.5 mm, less than 0.4 mm, less than 0.3 mm, less than 0.2 mm, less than 0.1 mm.

In some embodiments, X-rays are generated by placing radioactive sources inside the patient on a temporary or permanent basis. In some embodiments, a nanoparticle composition is injected along with the implantation of a radioactive source.

The radiation dosage regimen is generally defined in terms of Gray (Gy) or Sieverts time and fractionation and can be carefully defined by the radiation oncologist. The amount of radiation a subject receives can depend on various considerations, such as the location of the tumor in relation to other critical structures or organs of the body, and the extent to which the tumor has spread. One illustrative course of treatment for a subject undergoing radiation therapy is a treatment schedule with a total dose of 5 Gy, 10 Gy, 15 Gy, 20 Gy, 25 Gy, 30 Gy, 35 Gy, 40 Gy, 45 Gy, 50 Gy, 55 Gy, 60 Gy, 65 Gy, 70 Gy, 75 Gy, or 80 Gy or any derivable range therein. The radiation dose can be administered to the subject in a single daily fraction of 1.0 Gy-2.0 Gy, 1.0 Gy-5.0 Gy, or 5.0 Gy-10.0 Gy 1 day a week, 2 days a week, 3 days a week, 4 days a week, or 5 days a week. A Gy is an abbreviation for Gray and refers to 100 rad of dose. Illustrative dosages used for photon-based radiation are measured in Gy, and in an otherwise healthy subject (that is, little or no other disease states present such as high blood pressure, infection, diabetes, etc.) for a solid epithelial tumor ranges from about 60 Gy to about 80 Gy, and for a lymphoma ranges from about 20 Gy to about 40 Gy. Illustrative preventative (adjuvant) doses are typically given at about 45 Gy to about 60 Gy in about 1.8 Gy to about 2 Gy fractions for breast, head, and neck cancers.

In some embodiments, the disease is cancer. In some embodiments, the disease is selected from the group including, but not limited to, a skin cancer, such as a melanoma; a connective tissue cancer, such as a sarcoma; an adipose cancer; a breast cancer; a head and neck cancer, such as a glioma; a lung cancer, such as mesothelioma; a stomach cancer; a pancreatic cancer; an ovarian cancer; a cervical cancer; a uterine cancer; an anogenital cancer, such as a testicular cancer; a kidney cancer; a bladder cancer; a colon cancer; a prostate cancer; a central nervous system (CNS) cancer; a retinal cancer; a blood cancer, such as leukemia; a neuroblastoma; multiple myeloma, and a lymphoid cancer, such as Hodgkin's or non-Hodgkin's lymphoma.

The method can comprise administering the MCL or a derivative and/or nanoparticle thereof to the subject at about the same time as, or later than the administration of the radiation. In some embodiments, the MCL or derivative and/or nanoparticle thereof can be administered to the subject prior to a dose or course of radiation.

In some embodiments, the method can further comprise administering to the subject an additional therapeutic agent or treatment. In some embodiments, the additional therapeutic agent or treatment is an immunotherapy agent or a cancer treatment selected from surgery, chemotherapy, toxin therapy, cryotherapy, and gene therapy. In some embodiments, the chemotherapy can be co-administered with the MCL or derivative thereof, e.g., in a nanoparticle comprising both MCL or a derivative thereof and a chemotherapeutic agent. In some embodiments, the additional therapeutic agent is an immunotherapeutic agent. In some embodiments, the additional therapeutic agent is an immune checkpoint inhibitor, such as, but not limited to, a PD-1 inhibitor, a PD-L1 inhibitor, a CTLA-4 inhibitor, an IDO inhibitor, a CCR7 inhibitor, an OX40 inhibitor, a TIM3 inhibitor, and a LAG3 inhibitor.

The additional therapeutic agent or treatment can be administered prior to, at the same time as, or later than the administration of the MCL or derivative and/or nanoparticle thereof. For example, in some embodiments, administration of MCL or a derivative thereof alone, or of MCL or a derivative thereof in combination with X-ray irradiation treatment, can be performed prior to surgery to reduce the size of a tumor.

In some embodiments, the presently disclosed subject matter provides a method comprising treating a disease in a subject in need thereof, the method comprising: (i) administering to the subject MCL or a derivative and/or nanoparticle thereof and (ii) administering to the subject a chemotherapeutic agent, an immunotherapy agent, or radiotherapy. In some embodiments, the method comprises administering the MCL or derivative thereof and an immunotherapy agent. In some embodiments, the method comprises administering to the subject a nanoparticle comprising MCL or a derivative thereof. In some embodiments, the subject is a mammal. In some embodiments, the subject is a human.

In some embodiments, the disease is cancer. In some embodiments, the disease is selected from the group including, but not limited to, a skin cancer, such as a melanoma; a connective tissue cancer, such as a sarcoma; an adipose cancer; a breast cancer; a head and neck cancer, such as a glioma; a lung cancer, such as mesothelioma; a stomach cancer; a pancreatic cancer; an ovarian cancer; a cervical cancer; a uterine cancer; an anogenital cancer, such as a testicular cancer; a kidney cancer; a bladder cancer; a colon cancer; a prostate cancer; a central nervous system (CNS) cancer; a retinal cancer; a blood cancer, such as leukemia; a neuroblastoma; multiple myeloma, and a lymphoid cancer, such as Hodgkin's or non-Hodgkin's lymphoma.

In some embodiments, the immunotherapeutic agent is an immune checkpoint inhibitor, such as, but not limited to, a PD-1 inhibitor, a PD-L1 inhibitor, a CTLA-4 inhibitor, an IDO inhibitor, a CCR7 inhibitor, an OX40 inhibitor, a TIM3 inhibitor, and a LAG3 inhibitor. In some embodiments, the immunotherapeutic agent can be formulated in the same pharmaceutical composition as the MCL or derivative and/or nanoparticle thereof or be part of (e.g., embedded in or attached to) the same nanoparticle as the MCL or derivative thereof.

In some embodiments, the method further comprises administering to the subject a chemotherapeutic agent. In some embodiments, the chemotherapeutic agent can be provided in a nanoparticle, such as a nanoparticle further comprising the MCL or derivative thereof. In some embodiments, the chemotherapeutic agent is selected from the group including, but not limited to, a platinum complex, such as cisplatin, oxaliplatin, carboplatin, or a prodrug thereof; doxorubicin; daunorubicin; docetaxel; mitoxanthrone; paclitaxel; digitoxin; gemcitabine; methotrexate; leucovorin; pemetresed disodium; vinblastine; vincristine; vindesine; cytarabine; azathioprine; melphalan; imitnib; anastrozole; letrozole; etoposide; vinorelbine; digoxin, and septacidin.

In some embodiments, the presently disclosed subject matter provides a method of treating a disease (e.g., cancer) in a subject in need thereof, wherein the method comprises: (i) administering to the subject MCL or a derivative and/or nanoparticle thereof; (ii) administering to the subject an immunotherapeutic agent (e.g., an immune checkpoint inhibitor); and (iii) irradiating at least a portion of the subject with ionizing radiation, such as with x-rays and/or protons. In some embodiments, the method can further comprise an additional therapeutic agent or treatment selected from the group including, but not limited to, surgery, toxin therapy, cryotherapy and gene therapy.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

Combinations of Micheliolide and Radiotherapy 1.1. In Vitro Cytotoxicity Against Glioma Cells GL261:

GL261 cells were seeded onto 96-well plates at a density of 2000 cells/well and treated with various concentrations of the dimethylamino Michael adduct of MCL (dimethylamino micheliolide, DMAMCL) for 24 hours to allow for sufficient cellular uptake and conversion to MCL before irradiation. The cells were irradiated with varying amounts of X-ray irradiation and then incubated for an additional 24 hours. The culture medium was exchanged with fresh medium and further incubated for an additional 48 hours. The cell viability was then detected by (3-(4,5-dimethylthiazol-2-yl)-5-(3-carboxymethoxyphenyl)-2-(4-sulfophenyl)-2H-tetrazolium) (MTS) assay (Promega, Madison, Wisconsin, United States of America).

At doses up to 10 µM DMAMCL or 8 Gy irradiation, monotherapy DMAMCL or irradiation showed little to no toxicity. However, cells treated with 1 µM or 10 µM DMAMCL and X-ray irradiation of 8 Gy irradiation showed significant cytotoxicity that far exceeded the additive effects of either therapy alone. See FIG. 1.

Figure 2:
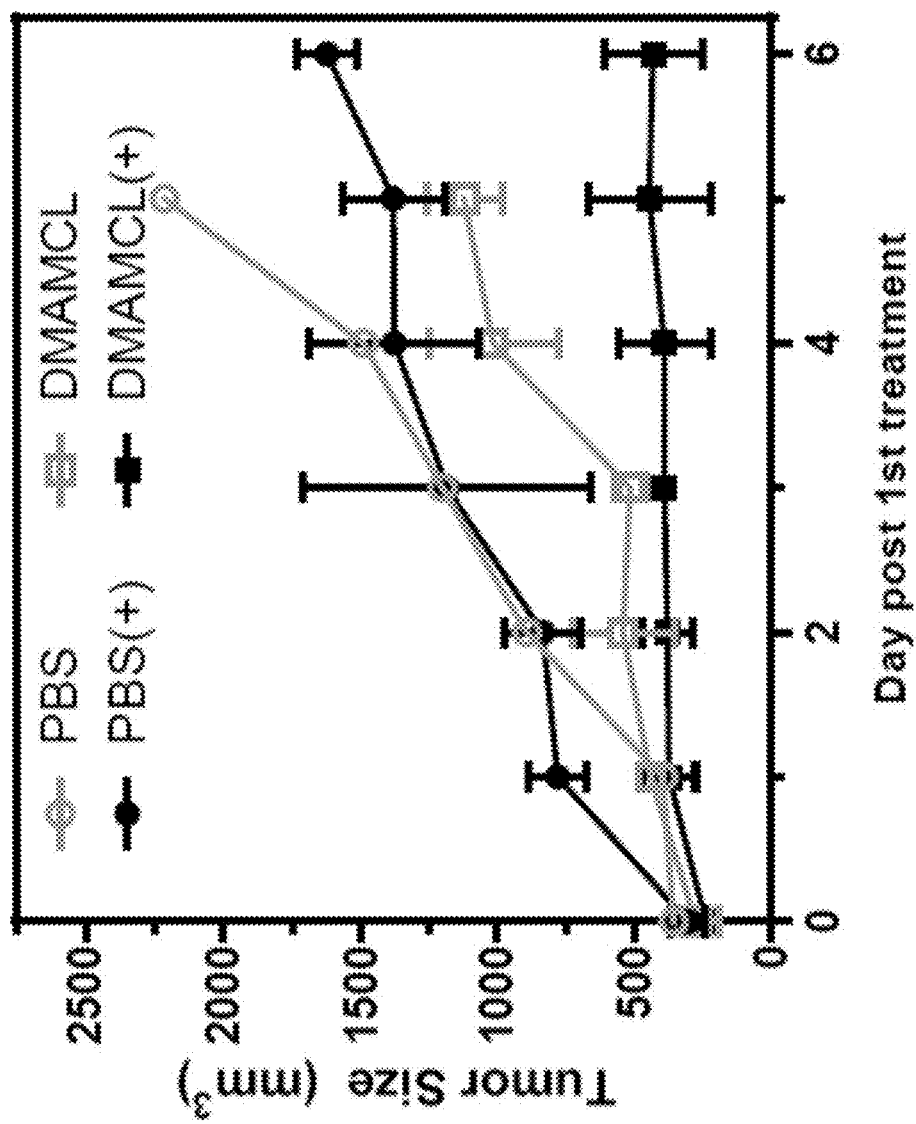
FIG. 2 is a graph showing the in vivo antitumor efficacy of combinations of dimethylamino micheliolide (DMAMCL) and irradiation in a mouse glioma 261 (GL261) tumor model in immunocompromised mice. Mice were orally dosed with 50 milligrams per kilogram (mg/kg) DMAMCL or with phosphate buffered saline and irradiated or not irradiated with a 4 gray (Gy) irradiation dose about 4 hours later every day for up to 7 days. Data for mice treated with PBS and not irradiated (PBS) is shown in open circles, data for mice treated with PBS and radiation (PBS (+)) is shown in filled circles, data for mice treated with DMAMCL and not irradiated is shown in open squares, and data for mice treated with DMAMCL and radiation (DMAMCL (+)) is shown in filled squares. Tumor size was measured in cubic millimeters (mm$^3$).

1.2. In Vivo Antitumor Activity:

The combination of DMAMCL and irradiation was evaluated on the glioma GL261 tumor model on immunocompromised Rag2$^{-/-}$ C57BL/6 mice. See FIG. 2. The mice were orally dosed with 50 mg/kg DMAMCL or PBS daily and irradiated with 4 Gy irradiation approximately 4 hrs after dosing, as applicable, for up to 7 days, starting when the tumors reached about 2 mm$^3$-300 mm$^3$. A Precision X-ray X-RAD 225 Image Guided Biologic Irradiator (Precision X-Ray Irradiation, North Branford, Connecticut, United States of America) was used for all animal studies. The instrument was set at 225 peak kilovoltage (kVp) and 13 milliampere (mA), with a 0.3 mm flat-board copper (Cu)

filter installed before a 15-mm collimator. The irradiation was given in two successive fractions with incident angles of 0° and 180° for each mouse.

Fractionated irradiation allows for higher total doses of X-ray but showed little or no appreciable effects on tumor growth. Though DMAMCL alone initially suppressed tumor growth, the tumors were ultimately not significantly different in size compared to those treated with irradiation alone. These results are consistent with in vitro results which showed varied effects leading to high average cell viability with large deviation in cells and tumors treated with irradiation alone. In contrast, the combination of DMAMCL and irradiation successfully controlled tumor growth leading to relatively stable tumor sizes over the course of treatment.

Example 2

Combinations of Micheliolide, Radiotherapy and Immune Checkpoint Blockade

Figure 3:
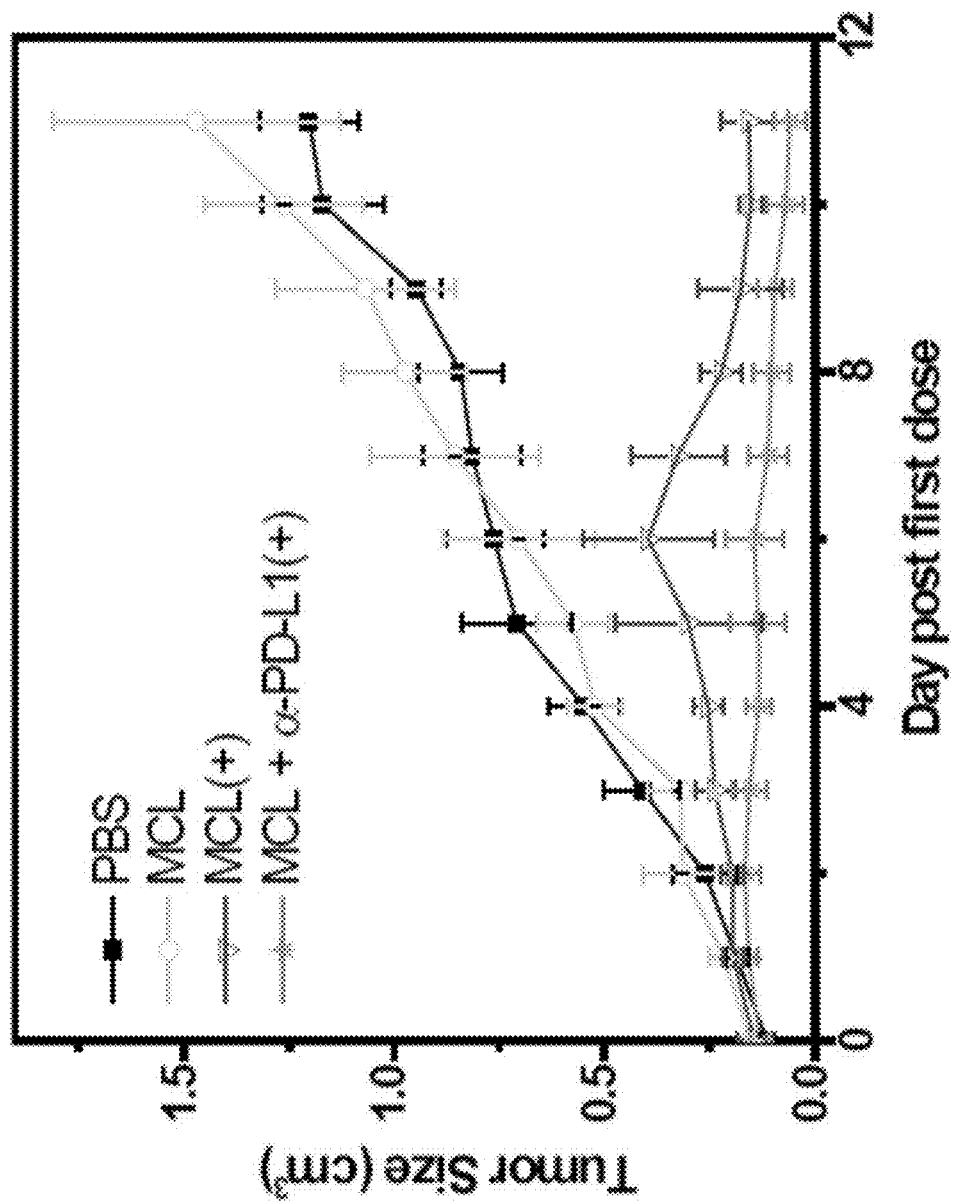
FIG. 3 is a graph showing the in vivo antitumor efficacy of combinations of micheliolide (MCL), irradiation, and an immunotherapy agent in a mouse glioma 261 (GL261) tumor model in immunocompetent mice. Mice were orally dosed with 50 milligrams per kilogram (mg/kg) MCL or phosphate buffered saline daily for up to 12 days. Some of the mice were irradiated with a 2 gray (Gy) irradiation dose about 4 hours after dosing with MCL. Some of the mice also received two 75 microgram (µg) doses of a programmed death ligand 1 (PD-L1) antibody on days 0 and 4. Data for mice treated with PBS and not irradiated (PBS) is shown in filled squares, data for mice treated with MCL and not irradiated is shown in open circles, data for mice treated with MCL and radiation (MCL (+)) is shown in open triangles, and data for mice treated with MCL, irradiation and antibody (MCL+α-PD-L1 (+)) is shown in open stars. Tumor size was measured in cubic centimeters (cm³).

The combination of DMAMCL, irradiation, and PD-L1 antibody was evaluated on the glioma GL261 tumor model on wildtype C57BL/6 mice. See FIG. 3. The treatment began 14 days after the inoculation of 2×10⁶ GL261 cells. The mice were orally dosed with 50 mg/kg DMAMCL or PBS daily and irradiated with 2 Gy irradiation approximately 4 hrs after dosing, as applicable, for up to 12 days, starting when the tumors reached ~150 mm³-200 mm³. One group of mice received two doses of 75 µg PD-L1 antibody on days 0 and 4. DMAMCL alone showed no effect on tumor growth, but combination with irradiation suppressed tumor growth and ultimately led to tumor regression. The combination of DMAMCL, irradiation, and a PD-L1 antibody controlled and regressed tumor growth immediately after treatment. By the cessation of treatment, 3/5 tumors treated with this combination were barely palpable. DMAMCL showed synergy with irradiation to control and regress GL261 tumors, which was further enhanced by combination with an immune checkpoint inhibitor.

Example 3

Nanoparticle-Based Micheliolide

Micheliolide and its derivatives can be formulated into nanoscale coordination polymers (NCPs) for use in treating multiple cancer types in combination with radiotherapy. Exemplary methods of preparing and using NCPs are described, for example in PCT International Patent Application Publication Nos. WO 2015/069926 and WO 2013/009701, U.S. Pat. No. 9,693,957, and U.S. Patent Application Publication No. 2016/0346204, the disclosures of each of which are incorporated herein by reference in their entireties. In some embodiments, according to the presently disclosed subject matter, MCL and its derivatives were loaded directly or as lipid-conjugates onto NCPs.

3.1. Synthesis of MCL Derivatives:

As shown in Equation 1 (Eq 1) of Scheme 1, below, micheliolide (500 mg, 2 mmol) was dissolved in 20 mL anhydrous dichloromethane (DCM). 2.5 mL dimethylamine 2M solution in tetrahydrofuran (THF) was added to the solution. The mixture was stirred at room temperature for 8 hours and then solvent was removed by rotary evaporation. The solid residue was purified by column chromatography using 5% methanol in DCM to obtain pure DMAMCL. ¹H-NMR (CDCl₃, 500 MHz): 1.32 (s, 3H), 1.70 (s, 3H), 1.82 (m, 2H), 2.06 (q, 1H), 2.19 (m, 4H), 2.27 (s, 6H), 2.41 (m, 2H), 2.62 (m, 2H), 2.67 (d, 2H), 2.72 (dd, 1H), 3.84 (t, 1H). ESI-MS: m/z=294.2 ([M+H]⁺, expected 294.2).

Scheme 1. Synthesis of MCL derivatives.

(Eq 1)

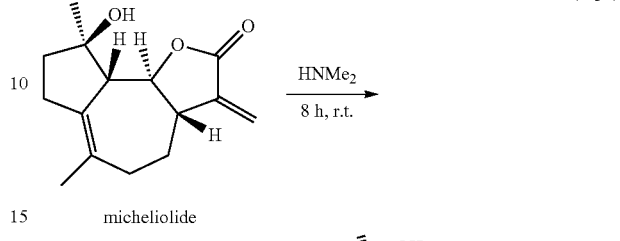

micheliolide dimethylamino micheliolide (Eq 2)

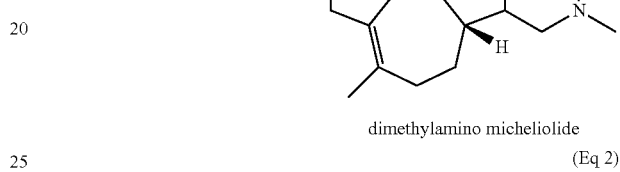

stearyl alcohol 1-(bromomethoxy)octadecane (Eq 3)

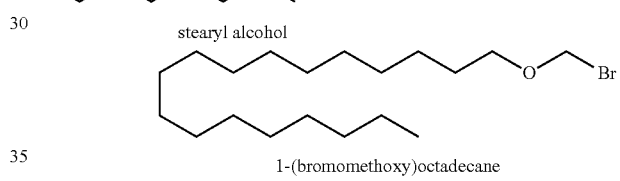

micheliolide

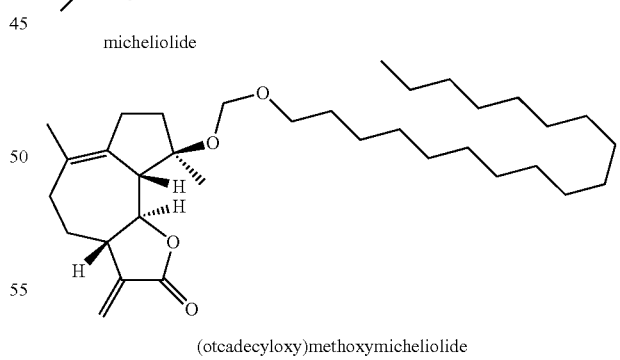

(otcadecyloxy)methoxymicheliolide

As shown in Equation 2 (Eq 2) of Scheme 1, above, stearyl alcohol (1.62 g, 6 mmol) and paraformaldehyde (180 mg, 6 mmol) was mixed in a dry round bottom flask. Bromotrimethylsilane (5 mL) was added drop-wise to the mixture and the solution was stirred at room temperature until all solid dissolved. Solvents was then removed by rotary evaporation to obtain crude 1-(bromomethoxy)octadecane.

As shown in Equation 3 (Eq 3) of Scheme 1, above, micheliolide (MCL, 500 mg, 2 mmol) was dissolved in anhydrous THF. Sodium hydride (NaH, 100 mg, 2.5 mmol) was added portion-wise to the mixture. 1-(Bromomethoxy)octadecane dissolved in anhydrous THF was added dropwise to the mixture and the mixture was stirred for 24 hours at room temperature. Solvents were removed and the solid residue was purified by column chromatography using 10% ethyl acetate (EtOAc) in hexanes to obtain (octadecyloxy)methoxymicheliolide. $^1$H-NMR (CDCl$_3$, 500 MHz): 0.91 (t, 3H), 1.30 (m, 26H), 1.38 (s, 3H), 1.57 (m, 4H), 1.74 (s, 3H), 1.87 (m, 2H), 2.09 (d, 1H), 2.25 (m, 3H), 2.43 (dd, 1H), 2.71 (t, 1H), 2.92 (d, 1H), 3.66 (m, 5H), 3.76 (t, 1H), 4.83 (d, 1H), 4.95 (d, 1H), 5.44 (d, 1H), 6.19 (d, 1H). ESI-MS: m/z=531.4 ([M+H]$^+$, expected 531.4)

Figure 4:
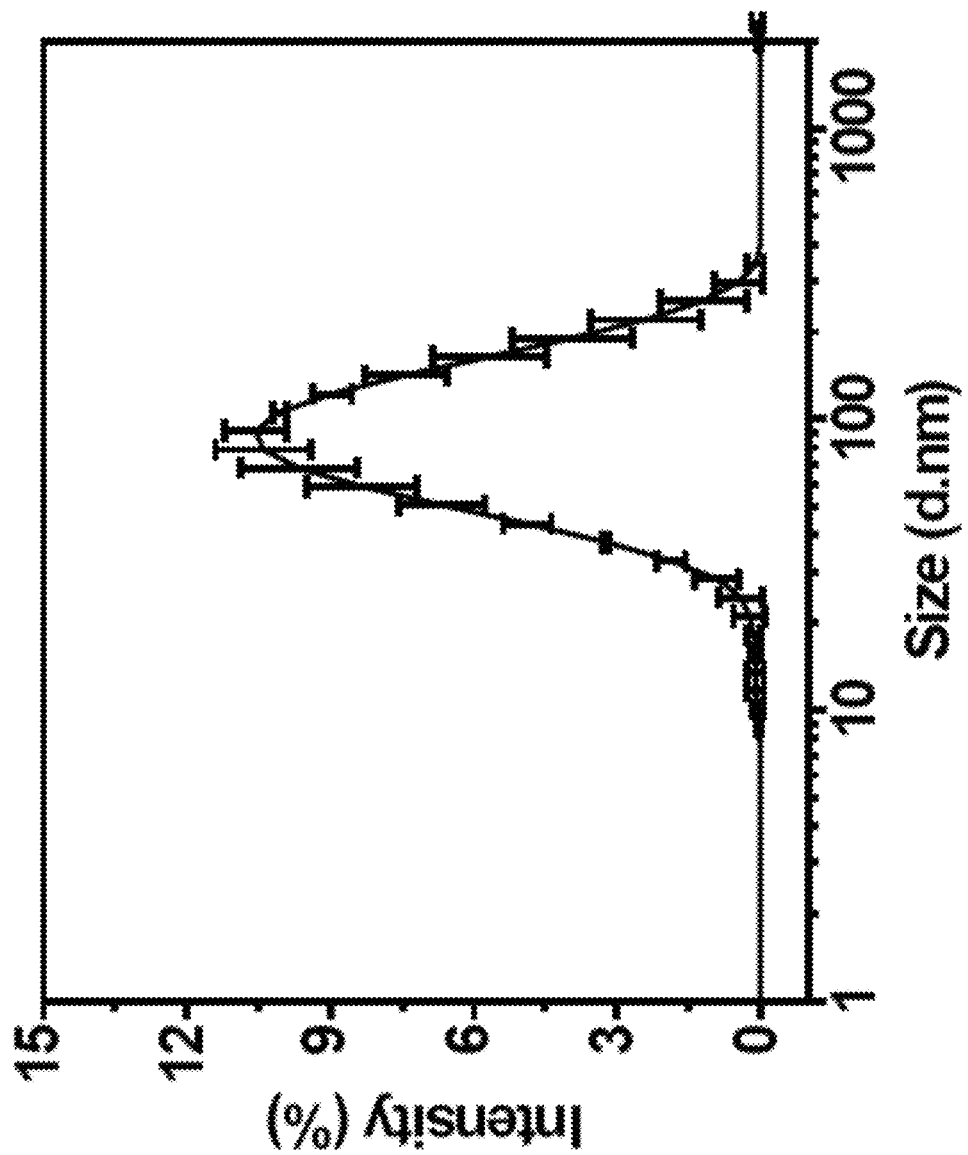
FIG. 4 is a graph showing the intensity plot (intensity (in percentage (%)) versus size (diameter in nanometers (d.nm))) of oxaliplatin-containing nano-coordination polymers (OxNCP) also comprising micheliolide (MCL) as measured using dynamic light scattering (DLS).

3.2. Loading of MCL onto Oxaliplatin (Ox)-Containing NCPs to Provide OxNCP/MCL:

OxNCP/MCL was obtained by adding a 80 µL THF solution of DOPC, cholesterol, MCL (molar ratio 3.5:2:3), DSPE-PEG2k (20 mol %) and OxNCP bare particles to 500 µL 30% (v/v) EtOH/H$_2$O at 50° C. THF and EtOH were evaporated and the solution was allowed to cool to room temperature before use. The particle size and distribution were determined by dynamic light scattering (DLS). See FIG. 4. OxNCP/MCL has a Z-average diameter of 76 nm.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method for treating a cancer in a subject in need thereof, the method comprising:
performing a first step, wherein the first step comprises administering to the subject dimethylamino micheliolide (DMAMCL) and a pharmaceutically acceptable carrier; and
performing a second step, wherein the second step comprises exposing at least a portion of the subject to ionizing irradiation energy.

2. The method of claim 1, wherein administering the DMAMCL comprises administering a nanoparticle selected from the group consisting of a polymeric micelle, a liposome, a dendrimer, an organic-based nanoparticle, a nanoscale coordination polymer particle, a nanoscale metal-organic framework particle, and an inorganic nanoparticle, wherein the DMAMCL is sequestered in the nanoparticle.

3. The method of claim 1, wherein the ionizing irradiation energy is X-rays or protons.

4. The method of claim 1, wherein the cancer is selected from the group consisting of a skin cancer, a connective tissue cancer, an adipose cancer, a breast cancer, a head and neck cancer, a lung cancer, a stomach cancer, a pancreatic cancer, an ovarian cancer, a cervical cancer, a uterine cancer, an anogenital cancer, a kidney cancer, a bladder cancer, a colon cancer, a prostate cancer, a central nervous system cancer, a retinal cancer, a blood cancer, a neuroblastoma, multiple myeloma, and a lymphoid cancer.

5. The method of claim 1, wherein the method further comprises administering to the subject an additional treatment selected from immunotherapy, surgery, chemotherapy, toxin therapy, cryotherapy and gene therapy.

6. The method of claim 5, wherein the additional treatment comprises immunotherapy.

7. The method of claim 6, wherein the immunotherapy comprises administering to the subject an immune checkpoint inhibitor.

8. The method of claim 7, wherein the immune checkpoint inhibitor is selected from the group consisting of a programmed death ligand 1 inhibitor and an indoleamine-2,3-dioxygenase inhibitor.

9. A method for treating a cancer in a subject in need thereof, the method comprising:
administering to the subject dimethylamino micheliolide (DMAMCL) and a pharmaceutically acceptable carrier;
administering to the subject a chemotherapeutic agent; and
exposing at least a portion of the subject to ionizing irradiation energy.

10. The method of claim 9, wherein administering to the subject DMAMCL comprises administering to the subject a nanoparticle selected from the group consisting of a polymeric micelle, a liposome, a dendrimer, an organic-based nanoparticle, a nanoscale coordination Polymer particle, a nanoscale metal-organic framework particle, and an inorganic nanoparticle, wherein the DMAMCL is sequestered in the nanoparticle.

11. The method of claim 9, wherein the cancer is selected from the group consisting of a skin cancer, a connective tissue cancer, an adipose cancer, a breast cancer, a head and neck cancer, a lung cancer, a stomach cancer, a pancreatic cancer, an ovarian cancer, a cervical cancer, a uterine cancer, an anogenital cancer, a kidney cancer, a bladder cancer, a colon cancer, a prostate cancer, a central nervous system cancer, a retinal cancer, a blood cancer, a neuroblastoma, multiple myeloma, and a lymphoid cancer.

12. The method of claim 9, wherein the method further comprises administering to the subject an immunotherapeutic agent.

13. The method of claim 12, wherein the immunotherapeutic agent is an immune checkpoint inhibitor.

14. The method of claim 9, wherein the method further comprises administering to the subject one or more of surgery, toxin therapy, cryotherapy and gene therapy.

15. The method of claim 1, wherein the administering of the first step is performed via oral administration, parenteral administration, or via administration directly to a tumor.

16. The method of claim 9, wherein the administering of the first step is performed via oral administration, parenteral administration, or via administration directly to a tumor.

* * * * *